(12) United States Patent  (10) Patent No.: US 8,484,807 B2
Malloy  (45) Date of Patent: Jul. 16, 2013

(54) NECKLACE WITH PLASTIC HAND HAVING A FRESH SCENT COMPARTMENT

(76) Inventor: Claude Malloy, Valley Stream, NY (US)

( * ) Notice: Subject to any disclaimer, the term of this patent is extended or adjusted under 35 U.S.C. 154(b) by 291 days.

(21) Appl. No.: 12/799,483

(22) Filed: Apr. 26, 2010

(65) Prior Publication Data

US 2011/0259048 A1    Oct. 27, 2011

(51) Int. Cl.
*A45F 5/00* (2006.01)
(52) U.S. Cl.
USPC .............. 24/3.4; 24/3.13; 224/148.5; 63/1.14
(58) Field of Classification Search
None
See application file for complete search history.

(56) References Cited

U.S. PATENT DOCUMENTS

| | | | | |
|---|---|---|---|---|
| D208,333 S | * | 8/1967 | Lincoln | D9/624 |
| 6,644,513 B1 | * | 11/2003 | Nesbitt | 222/175 |
| 6,907,877 B2 | * | 6/2005 | Balogh, II | 128/200.24 |
| 8,082,754 B2 | * | 12/2011 | Kazazian | 63/1.15 |
| 2007/0012727 A1 | * | 1/2007 | Licari | 222/167 |
| 2009/0272146 A1 | * | 11/2009 | Kazazian | 63/1.14 |

* cited by examiner

*Primary Examiner* — Jack W. Lavinder

(57) ABSTRACT

A necklace with plastic hand having a fresh scent compartment includes a 36 inch nylon lanyard necklace made to go around the user's neck; plus a refillable new plastic hand device with two circular plastic hang tabs assembled together and attached onto the palm area. The new plastic hand device is for storing a fresh scent liquid-gel hand sanitizer inside, so now any user of a new liquid-gel hand sanitizer has an easier way to try to keep their own personal hands cleaner and well sanitized from today's germs and viruses. Finally, the new nylon lanyard necklace w/swivel hook is fastened onto of the circular plastic hang tab assembly on the new plastic hand device to form a new compartment. In addition, the new plastic hand device has a screw on 15 mm snap-top cap with valve for releasing the liquid-gel hand sanitizer from the new plastic hand device into a user's hands for sanitizing.

1 Claim, 4 Drawing Sheets

NECKLACE WITH PLASTIC HAND HAVING A FRESH SCENT COMPARTMENT

BACKGROUND

The present invention relates generally to an instant hand sanitizer container and more specifically to a new necklace with plastic hand having a fresh scent compartment made for the purpose of hand sanitizing.

DESCRIPTION OF PRIOR ART

Washing hands is typically not practiced as frequently as desired or in a sufficient manner. Moreover, in many other developing countries, the sanitary and hygienic conditions at schools, childcare centers, hospitals, restaurants, group homes, supermarkets and other public facilities are often very poor, and can be characterized by the absence of properly functioning or existing water supply for sanitation or hand washing facilities. This is one main reason why, our present invention, a new necklace with plastic hand having a fresh scent compartment was designed to help remind every user to wash their hands in our public places. In this respect, every user of our new necklace with plastic hand having a fresh scent compartment will benefit & now began to have a smart, safe & sanitary way to greater improve the removal of bacteria, germs, fungus, & spores away from their hands.

SUMMARY OF THE INVENTION

The features of the present invention allow the user total control and repetitive use of the necklace with plastic hand having a fresh scent compartment. Since, their hands are constantly contaminated through the touch of any surface, the handing of an object; it makes it tough to keep fresh and well clean hands in our public places. The CDC reports that contaminated hands are a major vehicle for transmission of infection in our public places. For example, a student's bare hands are also a major element in the spread of germs & or infections in schools. The cost to the schools of absence is very high. Students can miss class time and carry illnesses home to their families. Hence, proper hand sanitation in the public school environment is also financially important to the schools, to the students and to the parents.

BRIEF DESCRIPTION OF THE DRAWINGS

The accompanying drawings illustrate various views and embodiments for carrying out the invention. In the drawings.

DETAILED DESCRIPTION OF THE INVENTION

Figure 1:
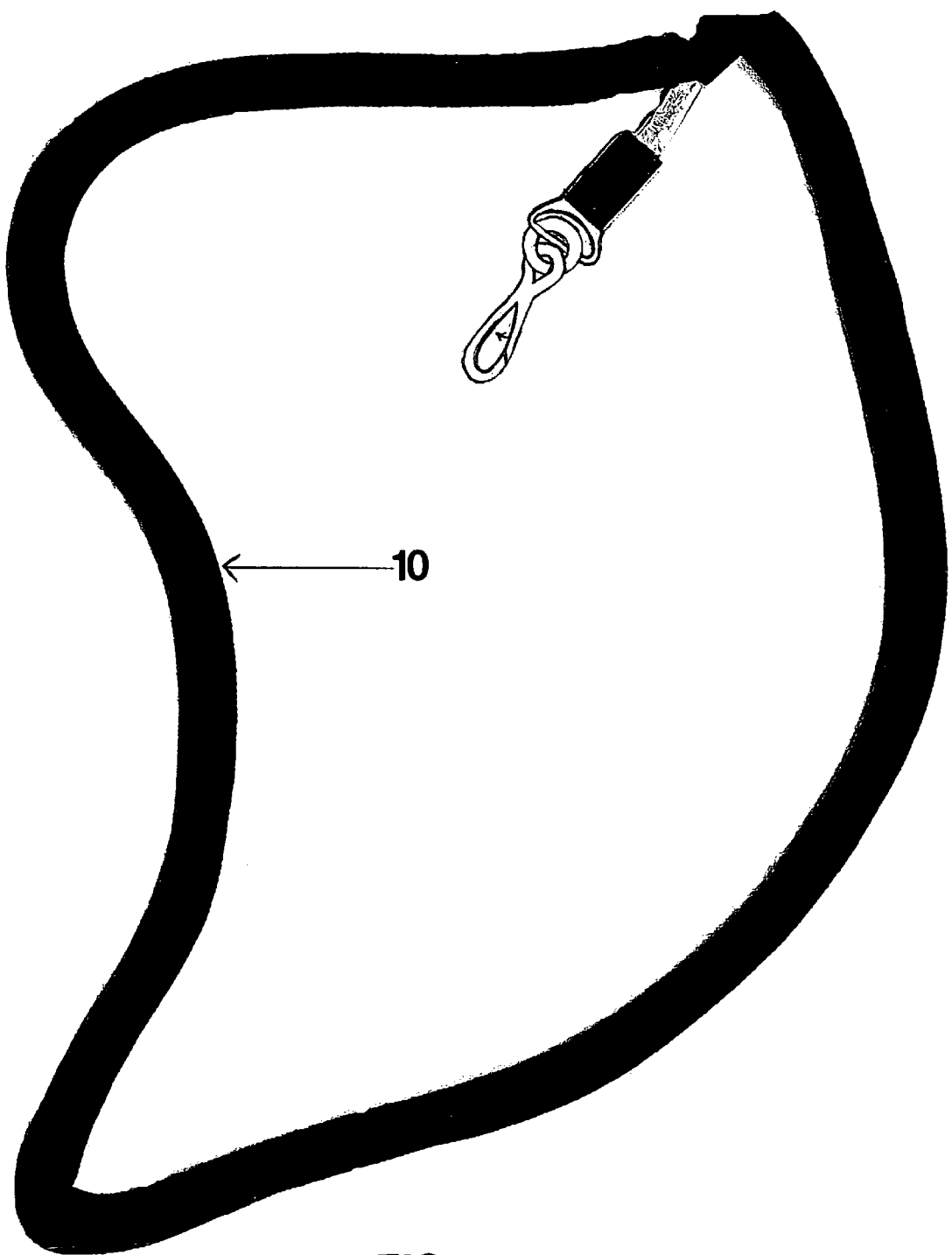
FIG. 1 is a view of a 36 inch nylon lanyard necklace before a refillable new plastic hand device is connected to it according to the present invention.
Figure 2:
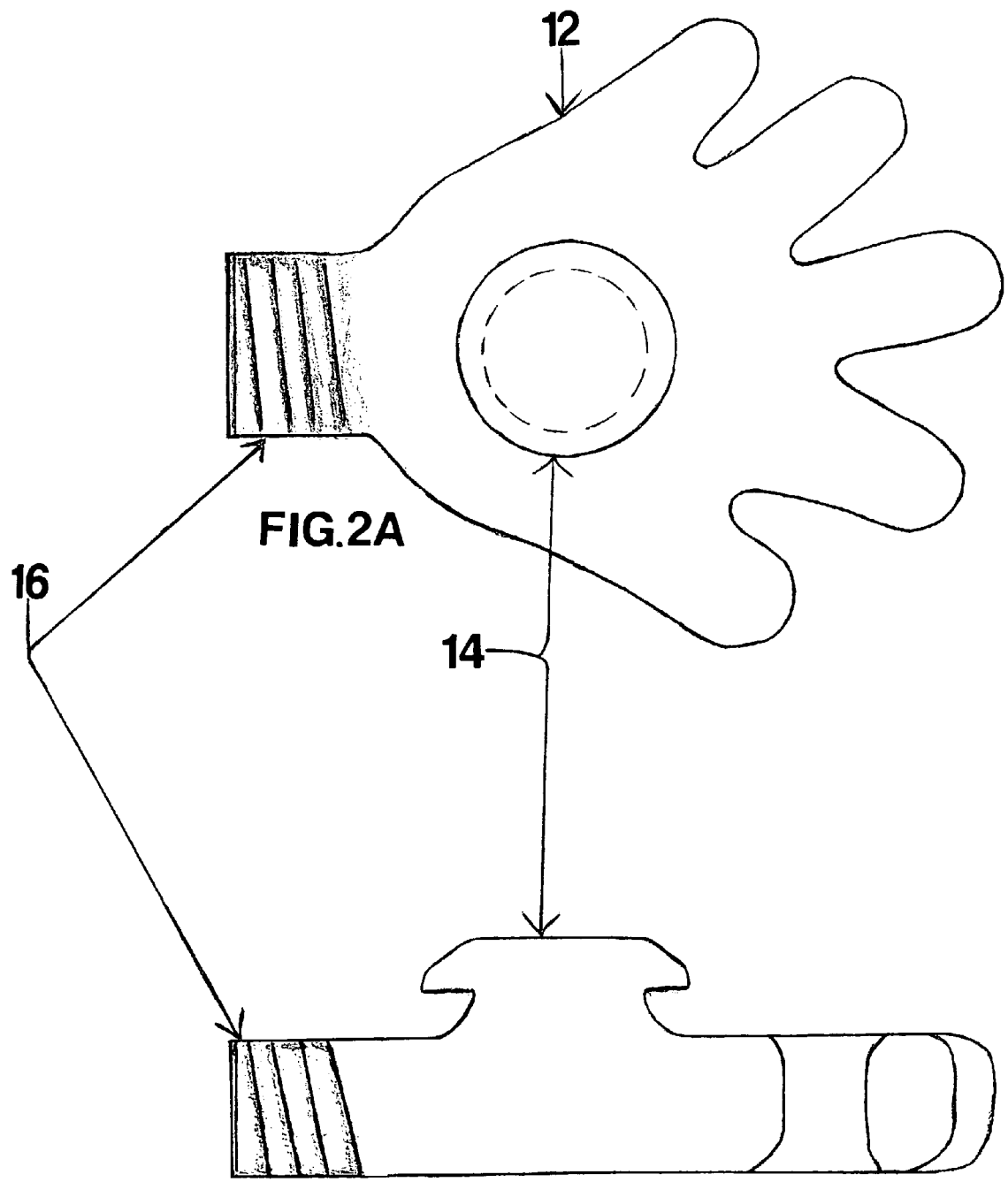
FIG. 2A is a back-side view of a refillable new plastic hand device designed with a smooth circular neck located on the palm area according to the present invention.
FIG. 2B is a bottom-side view of a refillable new plastic hand device designed with a neck with threads located on the wrist area according to the present invention.
Figure 4:
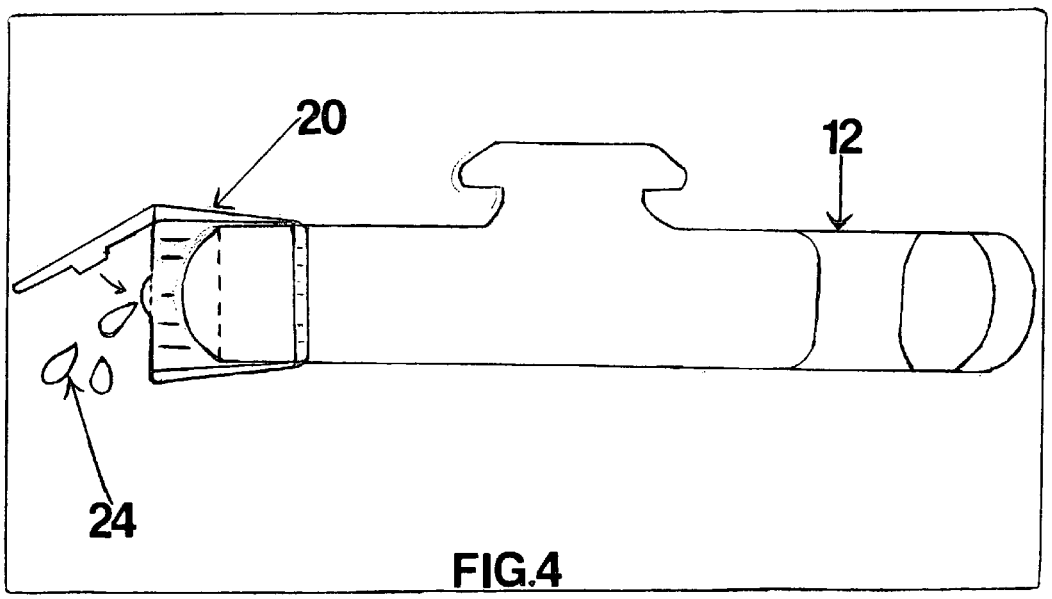
FIG. 4 is a bottom-side view of a new plastic hand with snap-top cap according to the present invention.
Figure 5:
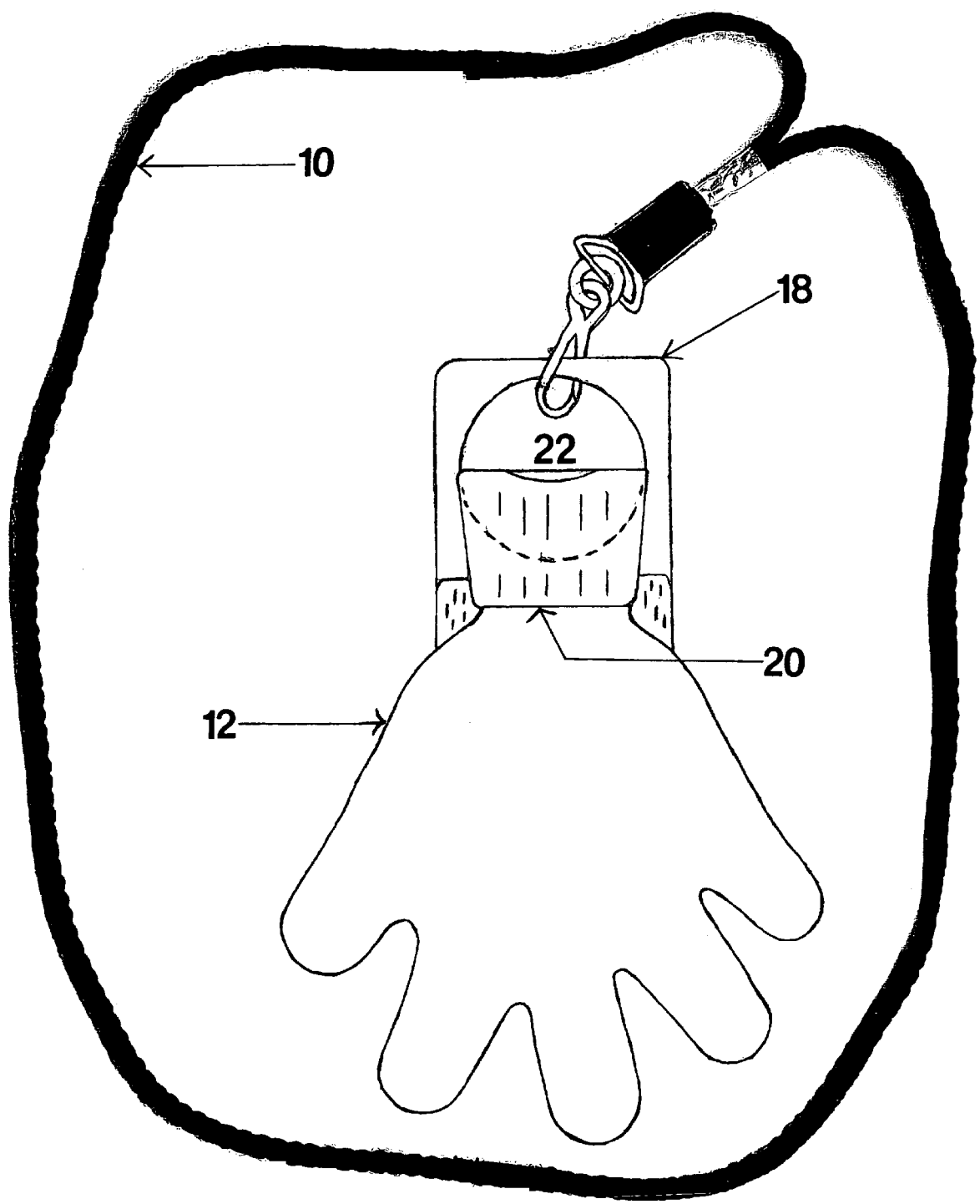
FIG. 5 is a complete-view of a necklace with plastic hand having a fresh scent compartment according to the present invention.

A necklace with plastic hand having a fresh scent compartment of the present invention is represented in FIGS. 2A, 4 & 5 by the reference numeral 12. In general, the 36 inch nylon lanyard necklace 10 and the new plastic hand device 12 were specially made to be placed together to form a new compartment 22. And as shown in FIGS. 2A and 2B, the new plastic hand device 12 has a ½ by ¼ inch circular neck 14 made in the middle of the palm area, and than another ½ by ½ inch neck w/threads 16 made on the wrist area of it.

Figure 3:
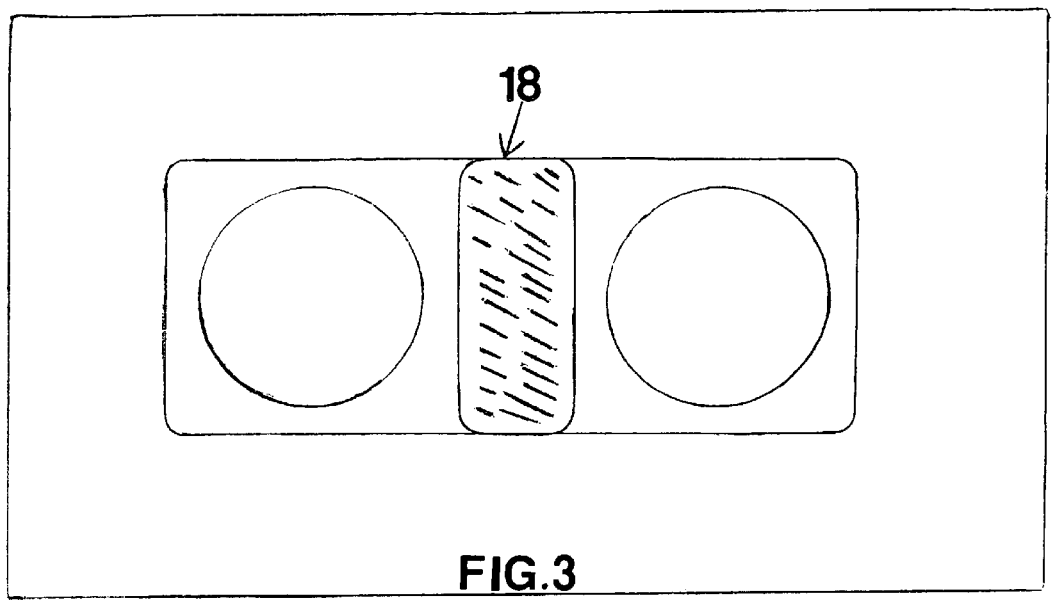
FIG. 3 is an actual-view of a circular plastic hang tab assembly according to the present invention.

Wherein, FIG. 3 is a drawing of a circular plastic hang tab assembly 18 made with two ½ inch holes on each end of it. Next, as shown in FIG. 4 of the drawings, we screw on the 15 mm snap-top cap 20 onto the matching threads 16 of new plastic hand device 12 and than manually put 15 mm snap-top cap 20 into an open valve position, press down on the middle of new plastic hand device 12 to release a fresh scent liquid 24 into a user's hands for proper hand washing according to the present invention.

Finally, in FIG. 5, we manually applied one of each of the following pieces; a 36 inch nylon lanyard necklace 10, plus a new plastic hand device 12, a new snap-top cap 20, and a circular plastic hang tab assembly 18, when placed together to form a necklace 10 with plastic hand 12 having a fresh scent compartment 22 according to the present invention.

What is claimed is:

1. A lanyard necklace assembly for attaching and carrying a compartment of fresh scent liquid-gel for hand sanitizing, comprising:

a necklace including a swivel hook;

a hand-shaped compartment formed from a plastic material including two neck portions, the first neck portion extending outwardly from the compartment and located in the middle of the palm area of said hand-shaped plastic compartment, said first neck portion is for attaching the compartment to a hang tab, and the second neck portion is located on the wrist area of the hand-shaped plastic compartment including threads for receiving a snap-top cap and a through-hole extending through the second neck portion into the interior of the compartment for receiving and dispensing the liquid-gel to and from the interior of the compartment;

a plastic hang tab including two adjacent apertures of substantially equal diameters, said first neck portion is positioned through said first aperture of said hang tab while the second aperture of said hang tab is located in one of two alternative positions, the first position of said second aperture is located on a side of said second neck portion in order to attach said swivel hook of said necklace thereto and the second position of said second aperture is located over and on the second neck portion when not attached to the swivel hook of the necklace, said second neck portion extending through said second aperture; and, a snap-top cap having threads thereon to mate with said threads on said second neck portion so as to secure said snap-top cap onto said compartment;

wherein a user can manually place said snap-top cap into an open valve position and then press downwardly on said plastic hand to release a fresh scent liquid-gel into their hands for sanitizing.

* * * * *